United States Patent
Hennigan

(10) Patent No.: US 7,056,309 B1
(45) Date of Patent: Jun. 6, 2006

(54) HYGIENIC CLEANSING AID

(76) Inventor: Michael Ross Hennigan, 7670 Chelsea Pl., Beaumont, TX (US) 77706

( * ) Notice: Subject to any disclaimer, the term of this patent is extended or adjusted under 35 U.S.C. 154(b) by 0 days.

(21) Appl. No.: 11/153,290

(22) Filed: Jun. 15, 2005

(51) Int. Cl.
*A61M 35/00* (2006.01)

(52) U.S. Cl. .................. 604/289; 604/290; 604/294

(58) Field of Classification Search ............. 604/289, 604/292, 290, 294
See application file for complete search history.

(56) References Cited

U.S. PATENT DOCUMENTS

| 3,409,010 | A | * | 11/1968 | Kron | 604/289 |
| 4,068,757 | A | * | 1/1978 | Casey | 206/363 |
| 5,196,244 | A | * | 3/1993 | Beck | 428/35.2 |
| 6,132,841 | A | * | 10/2000 | Guthrie et al. | 428/132 |
| 6,139,514 | A | * | 10/2000 | Benson | 602/63 |
| 6,647,549 | B1 | * | 11/2003 | McDevitt et al. | 2/21 |
| 6,905,487 | B1 | * | 6/2005 | Zimmerman | 604/292 |
| 2004/0019336 | A1 | * | 1/2004 | Temple et al. | 604/294 |

* cited by examiner

Primary Examiner—Tatyana Zalukaeva
Assistant Examiner—Ginger Chapman

(57) ABSTRACT

The invention is a hygienic cover for ones finger to prevent spreading microorganisms. The invention has an inner flexible microorganism impervious layer. Additionally, the invention would have an outer absorbent layer such as a cotton weave to absorb liquids and bond to mucus. Furthermore, the outer layer can contain and or the entire apparatus can be covered in antiseptic chemicals and or saline solutions to insure the outer layer is free of any microorganisms. Additionally, the invention would have one or more tabs that can be grasped by ones other hand to aid in the application and removal of the invention.

4 Claims, 1 Drawing Sheet

US 7,056,309 B1

HYGIENIC CLEANSING AID

| 6807681 | Oct. 26, 2004 | Sorrels | 2/21 |

FIELD OF THE INVENTION

The invention relates generally to the field of hygiene and more particularly to the field of the prevention of the spreading of microorganisms.

BACKGROUND OF THE INVENTION

Currently, there are many medications to treat the common cold but they only treat the symptoms they can not yet cure the common cold. There are vaccines to help prevent contagions such as Influenza. However, these methods are not always effective because people still get influenza even if they have had the vaccination because viruses constantly mutate. Recent medical studies have shown that many microorganisms such as the common cold, influenza and many others can be considered to be air born contagions, which means a carrier can infect another without making direct contact. However, the studies also show that in many cases the contagion is not spread from a carrier to another person through the air but by mutual contact of surfaces or objects. For example, a person with a common cold sneezes or blows their nose into a handkerchief. The mucus fluid of the nasal cavity is then mostly deposited onto the handkerchief. However, some small fragments of the mucus may escape in to the air. However, because the contagion is for the most part contained within the small fragments of mucus, which is mostly water they should quickly fall to the ground due to gravity. Unless someone was standing right next to the carrier when they sneezed or blew their nose it is unlikely the contagion would be The invention would be very beneficial to help prevent people from getting the common cold or influenza. However, it would also be a very effective tool to use against other microorganism outbreaks, such as SARS. The invention could be handed out to people in infectious areas to help stop the spread of a microorganism.

BRIEF SUMMARY OF THE INVENTION

The invention is a hygienic cover for ones finger that fits over the finger like the finger of a latex glove. The invention is to be worn over the finger to allow the use of the finger to clean parts of the body without spreading microorganisms. The invention has an inner flexible microorganism impervious layer, such as latex. Additionally, the invention would have an outer absorbent layer that has means to absorb moister and bond to mucus. Furthermore, the outer layer can contain and or the entire apparatus can be covered in antiseptic chemicals or saline solutions to insure the outer layer is free of any microorganisms. Additionally, the invention would have one or more tabs that can be grasped by ones other hand to aid in the application and removal of the invention. In addition, the invention can be individually packaged in a microorganism impervious package to insure that the invention is free of microorganisms at the time of use.

BRIEF DESCRIPTION OF THE DRAWINGS

The many objects and advantages of the present invention will become apparent to those skilled in the art when the following description of an example of the best mode for practicing the invention. When read in conjunction with the accompanying drawing. Wherein.

DETAILED DESCRIPTION OF THE PREFERRED EMBODIMENTS

Figure 1:
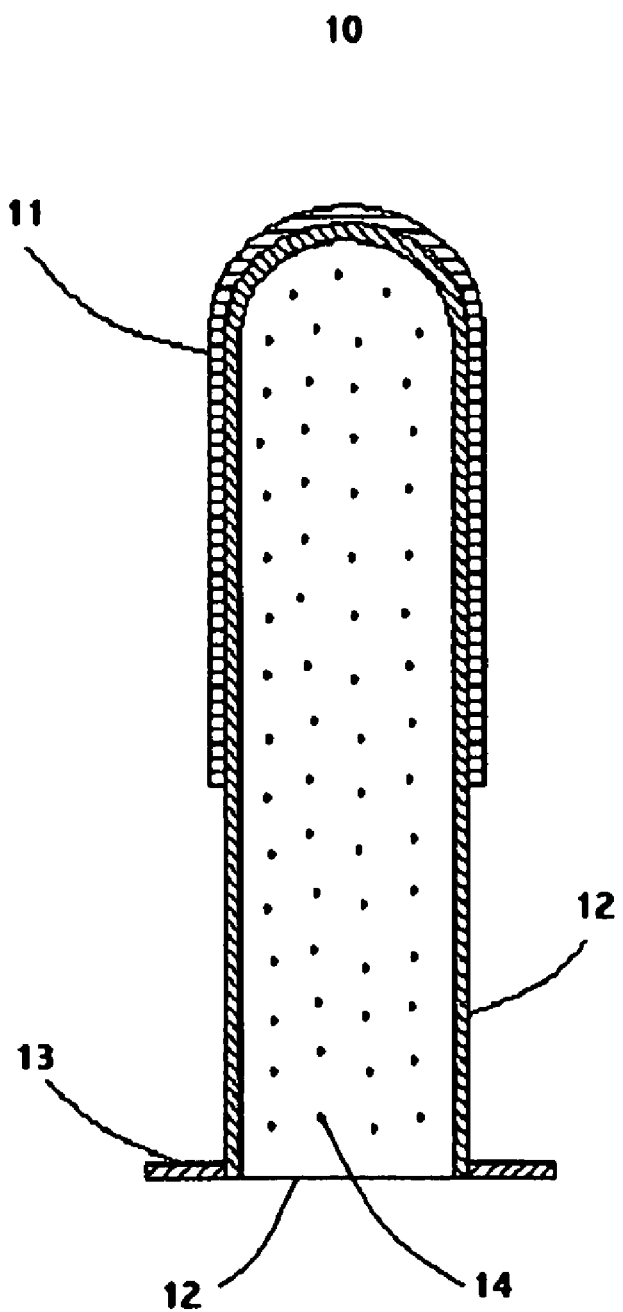
FIG. 1 is a top cross sectional view of all parts comprising the present invention.

The invention (10) is comprised of an inner layer (12) that has a form like a finger of a glove that fits snug about a finger and is constructed of a material that is flexible, stretchable, and resilient to tears and is impervious to microorganisms, such as latex. Additionally, the invention has an outer layer (11) that is bonded to the outside of said inner layer (12) and is constructed of a material or materials that are flexible, stretchable, textured, porous and has means to absorb liquids and adhere to mucus and or any other body secretions or parts, such as a cotton weave. Furthermore, said outer layer (11) can contain and or the entire apparatus can be covered in antiseptic chemicals or saline solutions to insure the invention is free of microorganisms at the time of use. Additionally, the invention has one or more tabs (13) that are connected to the inner layer (12) and can be grasped by ones other hand to aid in the application and removal of the invention. Additionally, the interior of the inner layer (12) can be coated with a layer of powder or lubricant (14) to aid in the application and removal of the invention. Furthermore, the invention can be made in various sizes to accommodate different size fingers. In addition, an individual invention or multiple inventions are packaged in a sealed microorganism impervious package so that the invention is free of microorganisms at the time the invention is used.

When a person needs to wipe there eyes, scratch their nasal cavity, remove access mucus form their nasal cavity or touch any other body orifice or body part. Then, the apparatus would be removed from the microorganism impervious packaging grabbing only the tabs. Then, the person would insert their finger into the hygienic cleansing aid like slipping on a glove. Then, the person could proceed to use the finger protected by the hygienic cleansing aid to wipe their eyes, nasal cavity or any other body orifice or body part without spreading any microorganism on the finger to another body part.

Other embodiments of the invention will be apparent to those skilled in the art. For example, the outer layer may cover various amounts of the inner layer. Additionally, the inner layer and the outer layer may be constructed of various types of materials and may have various thicknesses at various points. Thus, while the invention has been particularly shown and described with respect to the Preferred Embodiments, it will be understood by those skilled in the art that changes in the form and details may be made therein without departing from the scope and spirit of the invention. The invention may be embodied in other specific forms without departing from the spirit or essential characteristics thereof. The present embodiments are therefore to be considered in all respects as illustrative and not restrictive, the appended claims rather than by the foregoing description, and all changes which come within the meaning and range of equivalency of the claims are therefore intended to be embraced therein.

I claim:

1. A hygienic nasal cavity cleansing device that is adapted to provide a cover for a wearer's finger and clean the wearer's nasal cavity and eyes while preventing the spread of microorganisms from the wearer's finger, the device comprising:

a nonabsorbent inner layer having a hollow tubular form having a closed distal end and adapted to conform to the wearer's finger and constructed of material that is flexible, stretchable, resilient and resistant to tears and impervious to microorganisms;

the nonabsorbent inner layer further comprising one or more tabs formed about the proximal end, said tabs adapted to be grasped by the wearer; and an absorbent outer layer bonded to the outer surface of said inner layer and is constructed of a material that is flexible, stretchable, textured and porous and adapted to adhere to mucus and body secretions; and wherein the inner surface of the nonabsorbent inner layer is coated with a lubricant.

2. A hygienic nasal cavity cleansing device according to claim 1 wherein the outer layer contains and/or the entire device is covered in antiseptic chemicals and/or a saline solution to insure the device is free of microorganisms at the time of use.

3. A hygienic nasal cavity cleansing device according to claim 1 wherein the device is made in various sizes adapted to accommodate different size fingers.

4. A hygienic nasal cavity cleansing device according to claim 1 wherein an individual device or multiple devices are packaged in a sealed microorganism impervious package so that the device is free of microorganisms at the time the device is used.

* * * * *